(12) United States Patent
Uthgenannt et al.

(10) Patent No.: US 10,537,342 B2
(45) Date of Patent: Jan. 21, 2020

(54) X-RAY BASED CUTBLOCK POSITIONING JIG

(71) Applicant: Biomet Manufacturing, LLC, Warsaw, IN (US)

(72) Inventors: Brian A. Uthgenannt, Cricklade (GB); Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/650,198

(22) Filed: Jul. 14, 2017

(65) Prior Publication Data

US 2017/0311962 A1    Nov. 2, 2017

Related U.S. Application Data

(63) Continuation of application No. 15/424,267, filed on Feb. 3, 2017, now Pat. No. 9,750,514, which is a
(Continued)

(51) Int. Cl.
*A61B 17/58* (2006.01)
*A61F 2/00* (2006.01)
(Continued)

(52) U.S. Cl.
CPC ........ *A61B 17/1764* (2013.01); *A61B 17/154* (2013.01); *A61B 17/155* (2013.01); *A61B 17/157* (2013.01); *A61B 17/1703* (2013.01)

(58) Field of Classification Search
CPC combination set(s) only.
See application file for complete search history.

(56) References Cited

U.S. PATENT DOCUMENTS

| 4,703,751 A | 11/1987 | Pohl |
| 5,234,433 A | 8/1993 | Bert et al. |

(Continued)

FOREIGN PATENT DOCUMENTS

| CA | 2921034 C | 10/2016 |
| CN | 101790353 A | 7/2010 |

(Continued)

OTHER PUBLICATIONS

"U.S. Appl. No. 13/967,717, Notice of Allowance dated Feb. 18, 2015", 11 pgs.
(Continued)

*Primary Examiner* — Sameh R Boles
(74) *Attorney, Agent, or Firm* — Schwegman Lundberg & Woessner, P.A.

(57) ABSTRACT

A cut block positioning jig including a first alignment member, a second alignment member, and both first and second guide members. The first alignment member is movable towards and away from a patient's bone to which the positioning jig is mounted to arrange the jig at a predetermined position relative to the bone based on x-rays of the patient. The second alignment member is movable towards and away from the bone to arrange the jig at the predetermined position relative to the bone. The first and second guide members are configured to direct cut block support members to the bone to couple a cut block to the bone to provide the bone with patient-specific cuts.

19 Claims, 4 Drawing Sheets

Related U.S. Application Data continuation of application No. 14/746,104, filed on Jun. 22, 2015, now Pat. No. 9,597,097, which is a continuation of application No. 13/967,717, filed on Aug. 15, 2013, now Pat. No. 9,060,786.

(51) Int. Cl.
*A61B 17/60* (2006.01)
*A61B 17/17* (2006.01)
*A61B 17/15* (2006.01)

(56) References Cited

U.S. PATENT DOCUMENTS

| | | | |
|---|---|---|---|
| 9,060,786 | B2 | 6/2015 | Uthgenannt et al. |
| 9,597,097 | B2 | 3/2017 | Uthgenannt et al. |
| 9,750,514 | B2 | 9/2017 | Uthgenannt et al. |
| 2008/0275451 | A1* | 11/2008 | McAllister .......... A61B 17/155 606/87 |
| 2010/0042105 | A1 | 2/2010 | Park et al. |
| 2014/0148811 | A1 | 5/2014 | Reeve et al. |
| 2015/0051602 | A1 | 2/2015 | Uthgenannt et al. |
| 2015/0173774 | A1* | 6/2015 | Leslie ................. A61B 17/155 606/102 |
| 2015/0351781 | A1 | 12/2015 | Uthgenannt et al. |
| 2017/0143354 | A1 | 5/2017 | Uthgenannt et al. |

FOREIGN PATENT DOCUMENTS

| | | |
|---|---|---|
| CN | 105658157 A | 6/2016 |
| CN | 107343808 A | 11/2017 |
| EP | 1669033 A1 | 6/2006 |
| EP | 3391836 | 10/2018 |
| JP | 07508203 A | 9/1995 |
| JP | 08308857 A | 11/1996 |
| JP | 10507107 A | 7/1998 |
| JP | 2008529607 A | 8/2008 |
| JP | 2008534163 A | 8/2008 |
| JP | 2010531187 A | 9/2010 |
| JP | 2016529951 A | 9/2016 |
| JP | 2017077491 A | 4/2017 |
| WO | WO-2009001083 A1 | 12/2008 |
| WO | WO-2011001292 A1 | 1/2011 |
| WO | WO-2012040100 A2 | 3/2012 |
| WO | WO-2015023769 A1 | 2/2015 |

OTHER PUBLICATIONS

"U.S. Appl. No. 13/967,717, Response filed Jan. 26, 2015 to Restriction Requirement dated Nov. 24, 2014", 10 pgs.
"U.S. Appl. No. 13/967,717, Restriction Requirement dated Nov. 24, 2014", 8 pgs.
"U.S. Appl. No. 14/746,104, Corrected Notice of Allowance dated Dec. 7, 2016", 2 pgs.
"U.S. Appl. No. 14/746,104, Non Final Office Action dated May 17, 2016", 9 pgs.
"U.S. Appl. No. 14/746,104, Notice of Allowance dated Nov. 17, 2016", 7 pgs.
"U.S. Appl. No. 14/746,104, Preliminary Amendment filed Aug. 27, 2015", 7 pgs.
"U.S. Appl. No. 14/746,104, Response filed Apr. 13, 2016 to Restriction Requirement dated Feb. 19, 2016", 7 pgs.
"U.S. Appl. No. 14/746,104, Response filed Aug. 15, 2016 to Non Final Office Action dated May 17, 2016", 13 pgs.
"U.S. Appl. No. 14/746,104, Restriction Requirement dated Feb. 19, 2016", 8 pgs.
"U.S. Appl. No. 15/424,267, Notice of Allowance dated May 3, 2017", 9 pgs.
"U.S. Appl. No. 15/424,267, Preliminary Amendment filed Feb. 6, 2017", 7 pgs.
"Australian Application Serial No. 2014306666, First Examiner Report dated May 11, 2016", 2 pgs.
"Canadian Application Serial No. 2,921,034, Voluntary Amendment filed Feb. 10, 2016", 6 pgs.
"Chinese Application Serial No. 201480054252.0, Office Action dated Nov. 18, 2016", (W/ English Translation), 20 pgs.
"European Application Serial No. 14755314.3, Response filed Oct. 13, 2016 to Communication pursuant to Rules 161(1) and 162 EPC dated Apr. 7, 2016", 12 pgs.
"International Application Serial No. PCT/US2014/050920, International Preliminary Report on Patentability dated Feb. 25, 2016", 9 pgs.
"International Application Serial No. PCT/US2014/050920, International Search Report dated Oct. 16, 2014", 6 pgs.
"International Application Serial No. PCT/US2014/050920, Written Opinion dated Oct. 16, 2014", 7 pgs.
"Japanese Application Serial No. 2016-522741, Office Action dated Aug. 2, 2016", (W/ English Translation), 5 pgs.
"Japanese Application Serial No. 2016-522741, Response filed Oct. 21, 2016 to Office Action dated Aug. 2, 2016", (W/ English Translation), 14 pgs.
"Nanoblock®,and iBiock®", Praxim Smart Instruments, Basic Instrument Set, Minimally Invasive Fixations, [Online] retrieved from the internet: www.praxim.fr/Products, (Apr. 29, 2013), 4 pgs.
"OrthoSensor Surgical Instruments, Implantables, Analytics, and Technology", [Online] retrieved from the internet: www.orthosensor .com/products/orthosensor -surgical; www.orthosensor.com/products/orthosensor-implantables;www.orthosensor.com/products/orthosensor-analytics;www.orthosensor.com/technology, (May 23 2013), 5 pgs.
U.S. Appl. No. 13/967,717, U.S. Pat. No. 9,060,786, filed Aug. 15, 2013, X-Ray Based Cutblock Positioning Jig.
U.S. Appl. No. 14/746,104, U.S. Pat. No. 9,597,097, filed Jun. 22, 2015, X-Ray Based Cutblock Positioning Jig.
U.S. Appl. No. 15/424,267, filed Feb. 3, 2017, X-Ray Based Cutblock Positioning Jig.
"Chinese Application Serial No. 201480054252.0, Response filed Feb. 20, 2017 to Office Action dated Nov. 18, 2016", 5 pgs.
"Japanese Application Serial No. 2016-246695, Office Action dated Jan. 30, 2018", (W/ English Translation of Claims), 8 pgs.
"Japanese Application Serial No. 2016-246695, Response filed Apr. 27, 2018 to Office Action dated Jan. 30, 2018", (W/ English Translation of Claims), 11 pgs.
"European Application Serial No. 17193349.2, Extended European Search Report dated Sep. 25, 2018", 8 pgs.
"Chinese Application Serial No. 201710580246.4, Office Action dated Mar. 29, 2019", w English Translation, 12 pgs.
"European Application Serial No. 17193349.2, Response filed Apr. 24, 2019 to Extended European Search Report dated Sep. 25, 2018", 20 pgs.
"Chinese Application Serial No. 201710580246.4, Response filed Jul. 26, 2019 to Office Action dated Mar. 29, 2019", (W/ English Claims), 9 pgs.

* cited by examiner

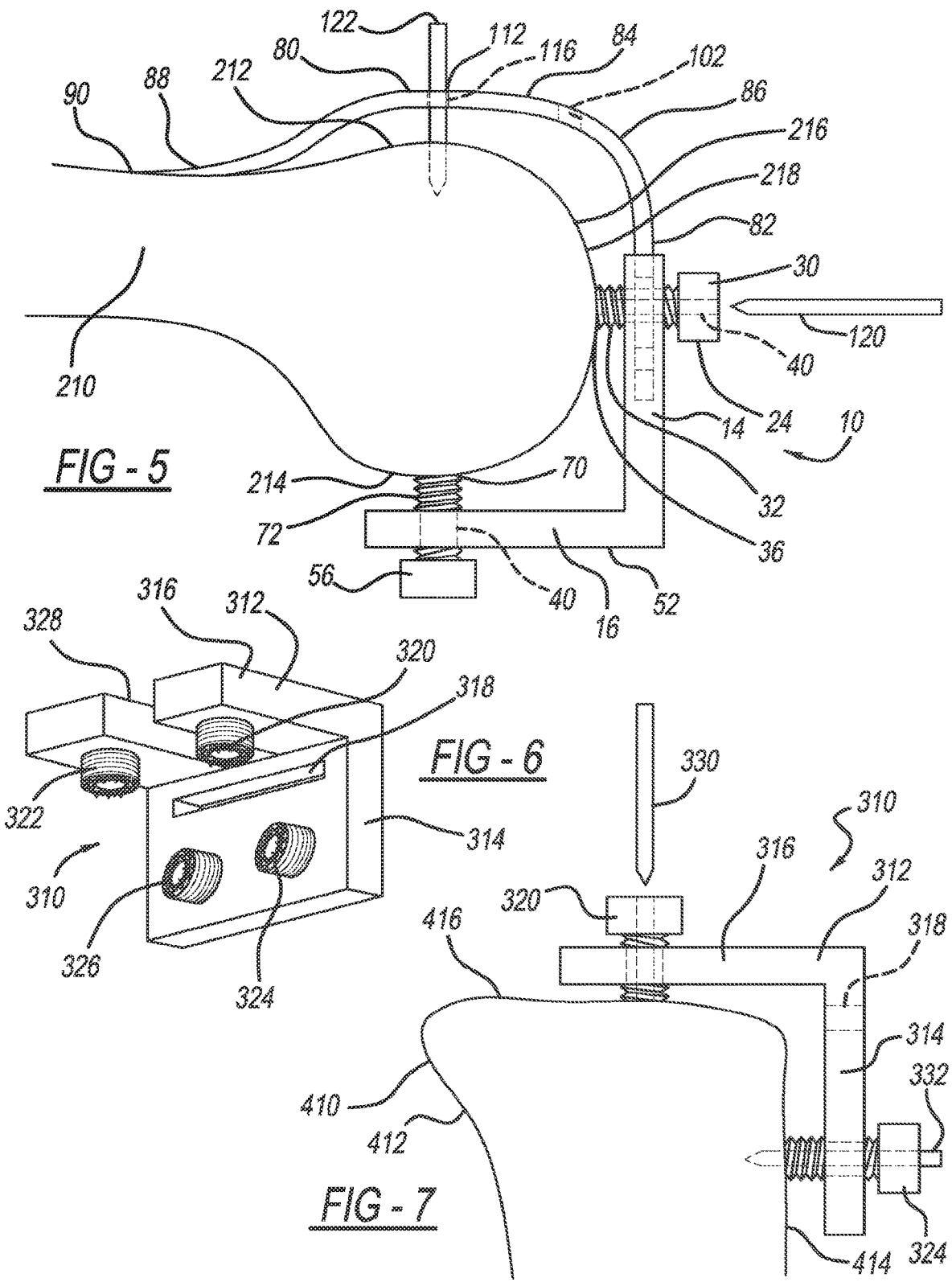

X-RAY BASED CUTBLOCK POSITIONING JIG

CROSS-REFERENCE TO RELATED APPLICATIONS

This application is a continuation of U.S. patent application Ser. No. 13/967,717 filed on Aug. 15, 2013. The entire disclosure of the above application is incorporated herein by reference.

FIELD

The present disclosure relates to a positioning jig for a cut block for cutting bone.

BACKGROUND

This section provides background information related to the present disclosure, which is not necessarily prior art.

To prepare a bone to receive an implant, the bone is often cut using a cut block. A cut block guide or positioning jig can be used to set the proper position of the cut block. The cut block guide can be custom designed to fit a particular patient's bone, and to set the position of the cut block based on the patient's specific anatomy. Such custom cut block guides are often based on timely and costly imaging modalities, such as CT and MRI imaging. For example, the CT and/or MRI image data is often analyzed by a physician and sent to a manufacturer, which makes the cut block guide and ships it to a physician or hospital for use during surgery. This process is costly and time consuming. A cut block guide that can be customized to fit a particular patient and guide a cutting instrument to the patient's bone to prepare the bone to accommodate the patient's particular anatomy would thus be desirable. A cut block guide that eliminates the need for an intramedullary rod would also be desirable.

SUMMARY

This section provides a general summary of the disclosure, and is not a comprehensive disclosure of its full scope or all of its features.

The present teachings provide for a cut block positioning jig including a first alignment member, a second alignment member, and both first and second guide members. The first alignment member is movable towards and away from a patient's bone to which the positioning jig is mounted to arrange the jig at a predetermined position relative to the bone based on x-rays of the patient. The second alignment member is movable towards and away from the bone to arrange the jig at the predetermined position relative to the bone. The first and second guide members are configured to direct cut block support members to the bone to couple a cut block to the bone to provide the bone with patient-specific cuts.

The present teachings further provide for a cut block positioning jig comprising a base, first alignment members, and second alignment members. The base includes a first portion and a second portion angled relative to the first portion. The first portion includes a first bone-facing surface and the second portion including a second bone-facing surface. The first alignment members are mounted to the first portion and movable to selectively position first bone engagement surfaces thereof at any one of a plurality of different distances from the first bone-facing surface to arrange the jig, and first guide members thereof, at a predetermined position relative to the bone. The second alignment members are mounted to the second portion and movable to selectively position second bone engagement surfaces thereof at any one of a plurality of different distances from the second bone-facing surface to arrange the jig at the predetermined position relative to the bone. The predetermined position is patient-specific and determined based on x-ray of a specific patient.

The present teachings also provide for a method for preparing a bone of a patient to receive an implant. The method includes determining bone cuts in the bone for positioning the implant in a patient-specific orientation based on an x-ray of the patient; and arranging a positioning jig on the bone at a predetermined position by setting alignment members of the jig at predetermined settings, the positioning jig is configured to direct fixation members to the bone sufficient to mount a cut block to the bone in a position suitable to guide a cutting device to the bone to make the predetermined bone cuts.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a side view of the femoral cut block positioning jig of FIG. 1 mounted to a femur;

FIG. 6 is a perspective view of a tibial cut block positioning jig according to the present teachings;

FIG. 7 is a side view of the tibial cut block positioning jig on a tibia.

Corresponding reference numerals indicate corresponding parts throughout the several views of the drawings.

DETAILED DESCRIPTION

Example embodiments will now be described more fully with reference to the accompanying drawings.

Figure 1:
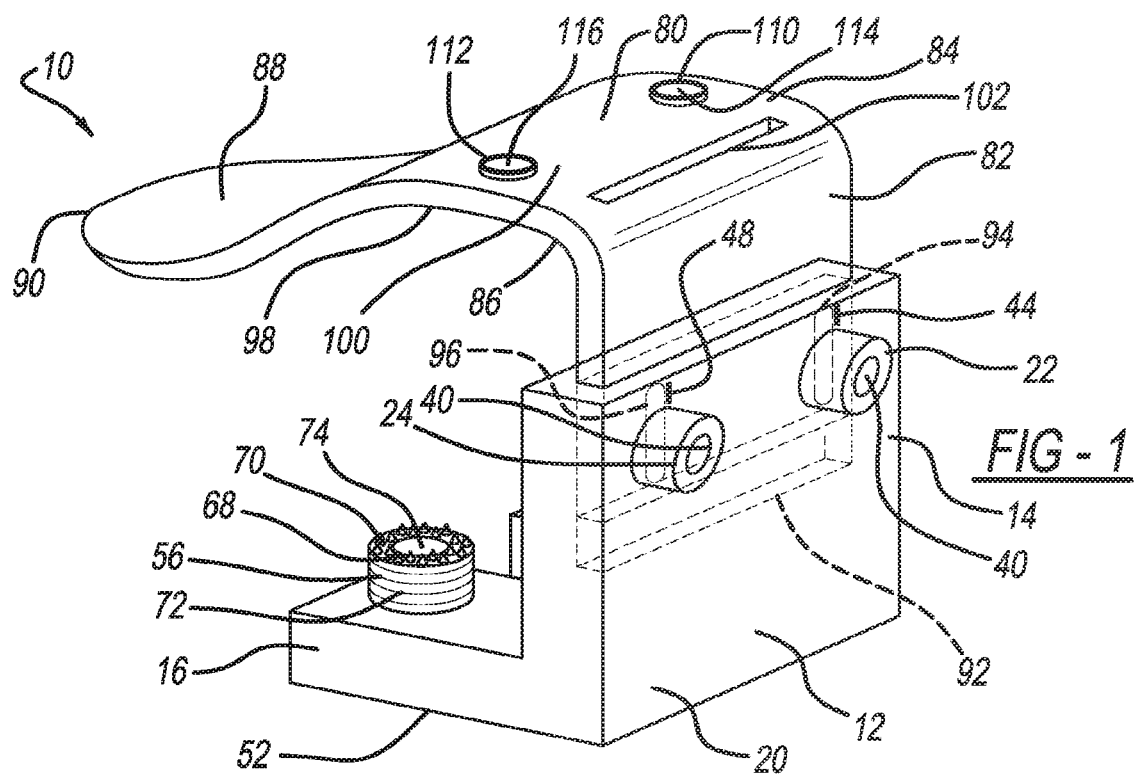
FIG. 1 is a perspective view of a femoral cut block positioning jig according to the present teachings.
Figure 2:
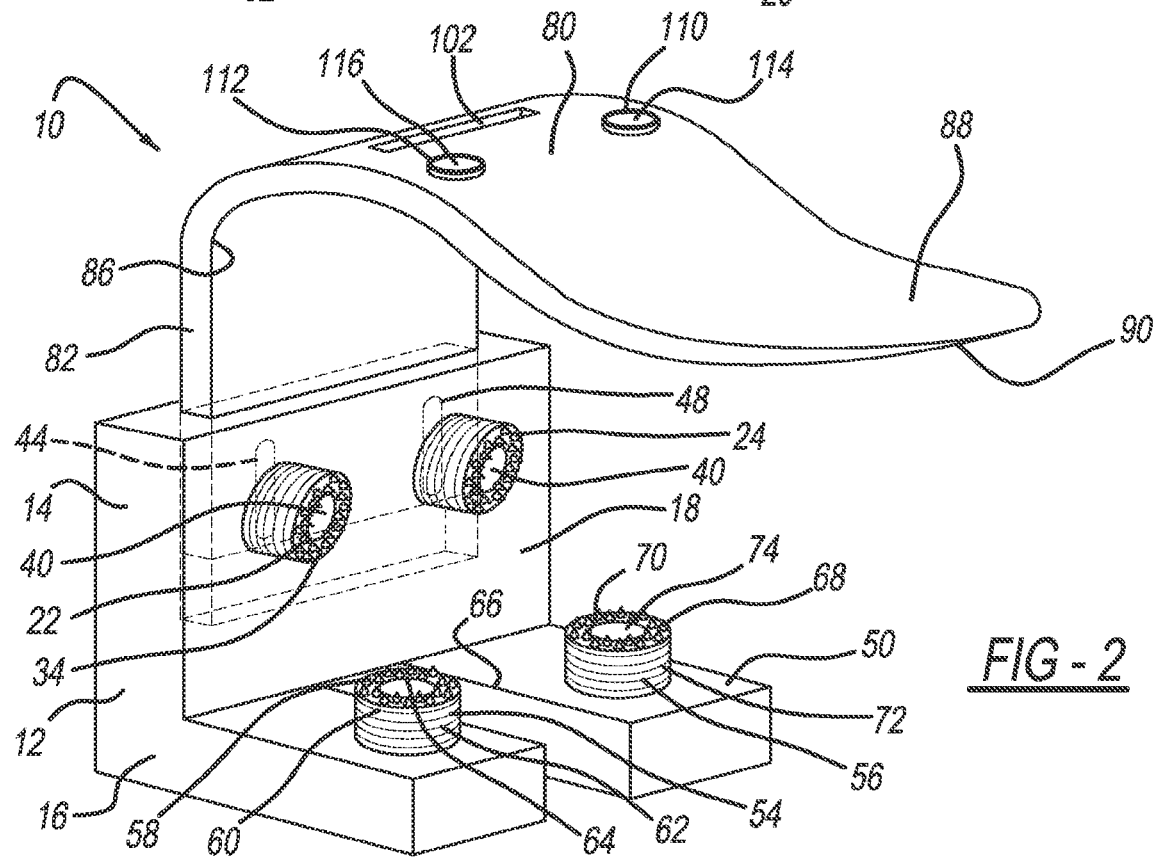
FIG. 2 is another perspective view of the femoral cut block positioning jig of FIG. 1.

With initial reference to FIGS. 1 and 2, a femoral positioning jig according to the present teachings is generally illustrated at reference numeral 10. The femoral positioning jig 10 is configured to position a cutting block on a femur for preparation of the femur to receive an implant. As described in detail herein, the femoral positioning jig 10 is reusable and adjustable to match the patient's anatomy based on x-ray images, for example. The femoral positioning jig 10 can be used in a total knee replacement procedure, or in a revision procedure.

The femoral positioning jig 10 generally includes a femoral base 12 having a first or distal portion 14, and a second or posterior portion 16. The distal and posterior portions 14 and 16 can be at any suitable angle relative to one another, such as at a right angle as illustrated. The femoral base 12 can be made of any suitably rigid material, such as a rigid metallic or polymer.

The distal portion 14 includes a first or bone-facing surface 18 and a second surface 20, which is opposite to the bone-facing surface 18. A first distal alignment member 22 and a second distal alignment member 24 are mounted to the distal portion 14. The first and second distal alignment members 22 and 24 extend through the distal portion 14, and can protrude from both the bone-facing surface 18 and the second surface 20, as illustrated in FIGS. 1 and 2 for example.

Figure 3:
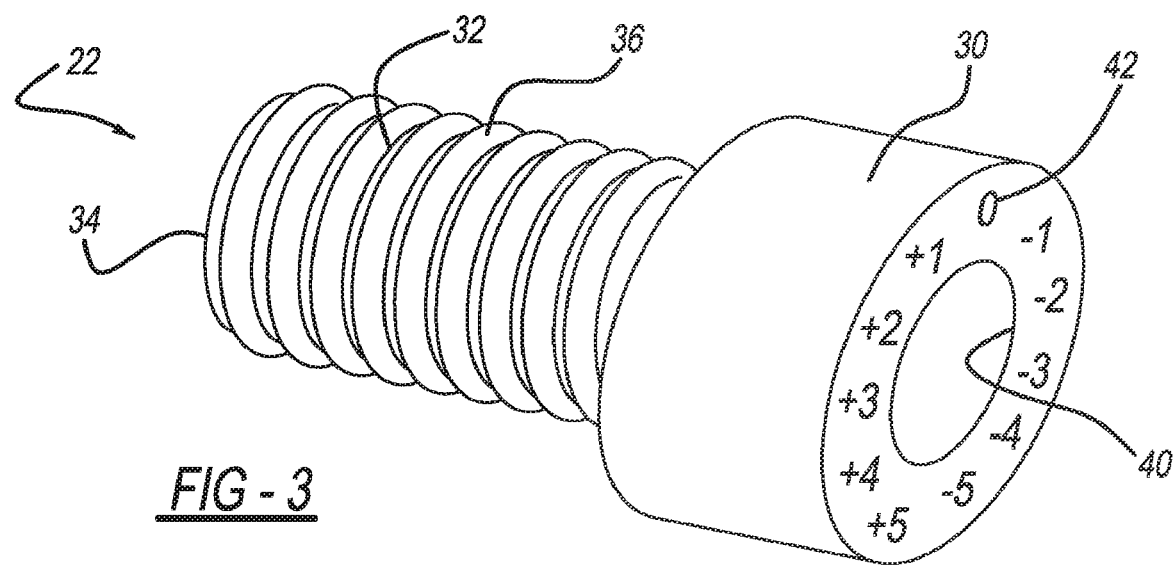
FIG. 3 is a perspective view of an alignment member of the femoral cut block positioning jig.
Figure 4:
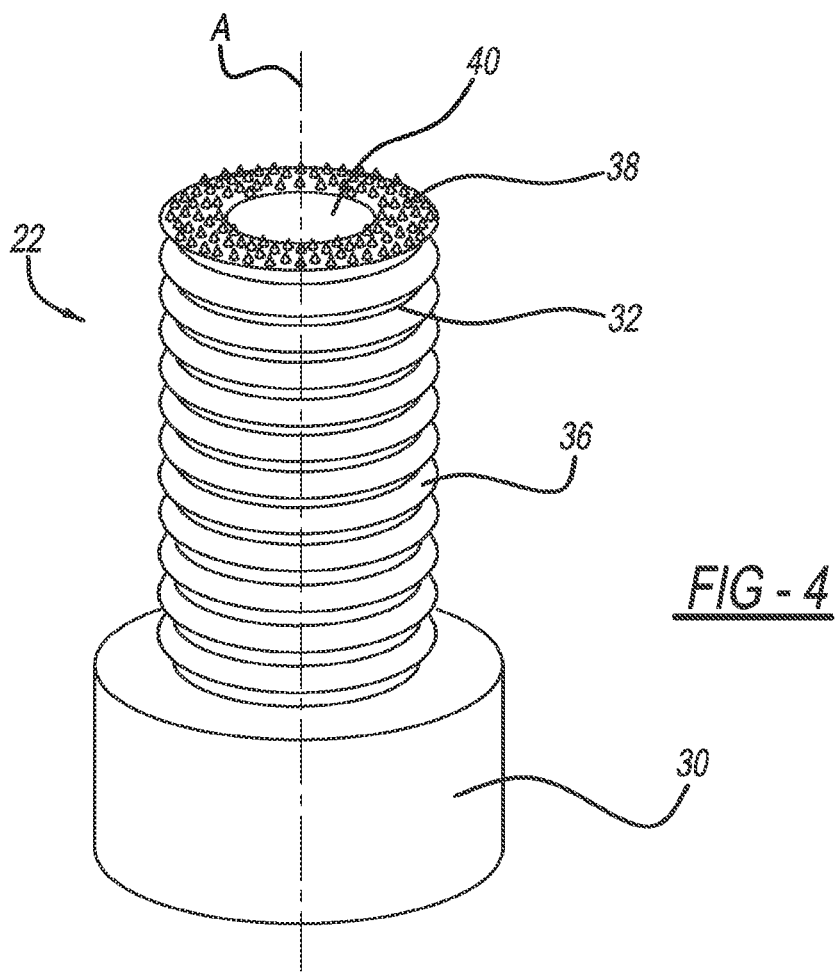
FIG. 4 is another perspective view of the alignment member of FIG. 3.

With continued reference to FIGS. 1 and 2 and additional reference to FIGS. 3 and 4, the first distal alignment member 22 can be an alignment dial including a head 30 and a shaft 32 extending from the head 30. The shaft 32 extends to a distal end 34 of both the shaft 32 and the overall first distal alignment member 22. The shaft 32 includes threads 36, which cooperate with threads (not shown) of the distal portion 14. Rotation of the first distal alignment member 22 in a first direction, such as clockwise, causes it to screw into the distal portion 14 so that the distal end 34 extends further from the bone-facing surface 18. Rotation of the first distal alignment member 22 in a second direction, such as counter-clockwise, causes the distal end 34 to move towards the bone-facing surface 18.

The first distal alignment member 22 includes a guide member 40, which is illustrated as a center bore defined by both the head 30 and the shaft 32. The guide member 40 extends along a longitudinal axis A (FIG. 4) of the first distal alignment member 22. As described herein, the guide member 40 is configured to guide fixation pins to the femur for mounting a cut guide to the femur. Although the guide member 40 is illustrated and described as defined by the first distal alignment member 22, the guide member 40 can be defined by any portion of the distal portion 14, or can be a separate device attached to the distal portion 14 or any portion of the femoral positioning jig 10.

At the distal end 34 of the first distal alignment member 22 are bone engagement members 38. The bone engagement members 38 can be any suitable device, formation, or surface features configured to securely engage the femoral bone that the femoral positioning jig 10 is coupled to. For example and as illustrated in FIG. 4, the bone engagement members 38 can be protruding sharpened or roughened portions, such as conical portions.

The first distal alignment member 22 further includes position indicators 42. The position indicators 42 can be at any suitable position on the first distal alignment member 22, such as on the head 30 as illustrated in FIG. 3. The position indicators 42 can be any suitable indicator or reference mark suitable to measure the rotational position of the first distal alignment member 22, such as numeric indicators on the head 30 as illustrated. Because the rotational position of the first distal alignment member 22 corresponds to the distance that the distal end 34 thereof extends from the bone-facing surface 18, the position indicators 42 also indicate the how far the distal end 34 is from the bone-facing surface 18.

The position indicators 42 can be referenced against any suitable marking or feature on the distal portion 14, such as reference mark 44 on the second surface 20 of the distal portion 14. For example, the first distal alignment member 22 can be configured such that when the position indicator 42 at "0" is aligned with the reference mark 44, the first distal alignment member 22 can be at a neutral position. Rotation of the first distal alignment member 22 clockwise such that the position indicator 42 at "+5" is aligned with the reference mark 44 can be the fully extended position of the first distal alignment member 22. In this fully extended position, the distal end 34 is at its furthest distance from the bone-facing surface 18. Rotation of the first distal alignment member 22 counter-clockwise such that the position indicator 42 at "−5" is aligned with the reference mark 44 can be the fully retracted position of the first distal alignment member 22. In this fully retracted position, the distal end 34 minimally extends from the bone-facing surface 18. The first distal alignment member 22 can be rotated to any intermediate position between "0" and the position indicators 42 at "+5" and "−5."

The second distal alignment member 24 can be similar to, or identical to, the first distal alignment member 22. Therefore, the second distal alignment member 24 can include its own position indicators 46 for referencing against reference mark 48 (FIG. 1) on the second surface 20 of the distal portion 14. The first and the second distal alignment members 22 and 24 can be selectively positioned on the femur to control the varus and valgus angle of the bone cuts, as well as the distal cut made through cutting slot 102 of the femoral positioning jig 10, as described in detail below.

With continued reference to FIGS. 1 and 2, the posterior portion 16 includes a first surface or bone-facing surface 50, and a second surface 52, which is opposite to the bone-facing surface 50. The posterior portion 16 defines a slot or clearance therein at reference numeral 66, which provides a clearance for ligaments. Mounted to the posterior portion 16 are a first posterior alignment member 54 and a second posterior alignment member 56. The first and the second posterior alignment members 54 and 56 can be located on opposite sides of the slot or clearance 66. The first and second posterior alignment members 54 and 56 can be similar to, or identical to, the first and the second distal alignment members 22 and 24.

The first posterior alignment member 54 includes bone engagement members 58 at distal end 60. Proximate to the distal end 60 are threads 62, which cooperate with threads (not shown) of the posterior portion 16. The first posterior alignment member 54 may optionally include a center bore 64 defined along a longitudinal axis thereof, and extending from the distal end 60 to a head (not shown) of the first posterior alignment member 54 that is similar to the head 30 of the first distal alignment member 22. The head of the first posterior alignment member 54 can also include the position indicators 42 described above in the description of the first distal alignment member for referencing off of one or more reference marks of the second surface 52.

The second posterior alignment member 56 is similar to the first posterior alignment member 54, and thus includes bone engagement features 68 at a distal end 70 thereof. The second posterior alignment member 56 further includes external threads 72, which cooperate with threads (not shown) of the second posterior portion 16. The second posterior alignment member 56 may optionally define a center bore 74 extending along a longitudinal axis thereof completely through the second posterior alignment member 56 from the distal end 70 to a head (not shown) at the second surface 52. The distal end 70 and the head are thus on opposite sides of the second posterior portion 16. The head of the second posterior alignment member 56 can also include the position indicators 42 described above in the description of the first distal alignment member 22 for referencing off of (one or more) reference marks of the second surface 52.

Each of the first and second posterior alignment members 54 and 56 can be rotated and operated in a manner similar to that described above with respect to the first and second distal alignment members 22 and 24, in order to position the distal ends 60 and 70 of the first and second posterior alignment members 54 and 56 respectively at a desired distance or height from the bone-facing surface 50 of the posterior portion 16. By selectively setting the first and the second posterior alignment members 54 and 56, the rotational position of the femoral positioning jig 10 can be set, as described herein. To facilitate setting the rotational orientation of the femoral positioning jig 10 and the femoral implant, the posterior portion 16 can include any suitable electronic alignment device, such as the OrthoSensor™ by OrthoSensor, Inc.

With continued reference to FIGS. 1 and 2, the femoral positioning jig 10 further includes an anterior portion 80. The anterior portion 80 generally includes a first anterior portion 82, a second anterior portion 84, a curved portion 86, and a stylus 88, which terminates at a tapered end 90. The first anterior portion 82 extends into a receptacle 92 defined by the femoral base 12, between the bone-facing surface 18 and the second surface 20 thereof. To accommodate the first and the second distal alignment members 22 and 24, the first anterior portion 82 includes cutouts 94 and 96 therein, which define slots positioned and sized to accommodate the first and second distal alignment members 22 and 24. The first distal alignment member 22 extends through the first cutout 94, and the second distal alignment member 24 extends through the second cutout 96.

The first anterior portion 82 extends out from within the receptacle 92 and transitions to the second anterior portion 84 at the curved portion 86, which is between the first and the second anterior portions 82 and 84. The second anterior portion 84 extends generally parallel to the second posterior portion 16. The stylus 88 extends from the second anterior portion 84 at a side thereof that is opposite to the first anterior portion 82. The second anterior portion 84 includes a first surface 98, which faces the second posterior portion 16, and a second surface 100, which is opposite to the first surface 98.

A cutting slot 102 is defined by the second anterior portion 84. The cutting slot 102 extends between the first and the second surfaces 98 and 100, and is configured to direct any suitable cutting instrument through the second anterior portion 84 to a femur that the femoral positioning jig 10 is seated on. The cutting slot 102 is illustrated as an elongated slot extending generally in the medial to lateral direction, but may be of any suitable shape or size, and at any suitable location to remove a distal portion of the femur in order to prepare the femur to receive an implant.

The anterior portion 80 includes a first anterior guide member 110 and a second anterior guide member 112. The first and the second anterior guide members 110 and 112 can be at any suitable position on the anterior portion 80, such as at the second anterior portion 84. Each of the first and second anterior guide members 110 and 112 extend through the second anterior portion 84, and can be any suitable guide members for guiding fixation pins to bone, as described herein. For example, the first and second anterior guide members 110 and 112 can be pinholes through the anterior portion 80 defining first and second center bores 114 and 116 respectively.

The anterior portion 80 can be adjusted by sliding the first anterior portion 82 into or out of the receptacle 92. For example, sliding the first anterior portion 82 into the receptacle 92 will bring the anterior portion 80 and the posterior portion 16 closer together. Sliding the anterior portion 80 such that the first anterior portion 82 extends further from within the receptacle 92 will increase the distance between the anterior portion 80 and the posterior portion 16. To maintain the anterior portion 80 and the posterior portion 16 spaced apart at a desired interval, the femoral positioning jig 10 can include any suitable locking or retention device.

With additional reference to FIG. 5, the femoral positioning jig 10 is illustrated coupled to a femur 210. The femur 210 generally includes an anterior surface 212, a posterior surface 214, and a distal or inferior surface 216. The femoral positioning jig 10 is positioned such that the anterior portion 80 is opposite to the anterior surface 212, the distal portion 14 is opposite to the distal surface 216 and condyles 218, and the posterior portion 16 is opposite to the posterior surface 214. The stylus 88 and the tapered end 90 thereof are arranged at the anterior surface 212 and abut the anterior surface 212. The curved portion 86 and the angle between the distal portion 14 and the posterior portion 16 allow the femoral positioning jig 10 to generally clip onto the femur 210. To accommodate larger femurs 210, the anterior portion 80 can be pulled away from the posterior portion 16 by sliding the first anterior portion 82 further out from within the receptacle 92 to increase the distance between the posterior portion 16 and the anterior portion 80. To accommodate smaller femurs 210, the anterior portion 80 can be moved closer to the posterior portion 16 by moving the first anterior portion 82 further into the receptacle 92.

The femoral positioning jig 10 is seated on the femur 210 such that the first and the second anterior guide members 110 and 112 are spaced apart from the femur 210. The first and the second distal alignment members 22 and 24 are positioned opposite to the distal surface 216 of the femur 210. The first and the second posterior alignment members 54 and 56 are positioned opposite to the posterior surface 214 of the femur 210. Generally, the alignment members 22, 24, 54, and 56 are initially set in a neutral position, such as at the position indicator 42 of "0". As described below, fixation members or pins 120 and 122 are not set until after alignment members 22, 24, 54, and 56 are set.

The first and the second distal alignment members 22 and 24, and the first and second posterior alignment members 54 and 56 are custom set for a particular patient based on x-rays of the patient in order to provide patient-specific cuts to the femur 210, thereby allowing the femoral implant to be aligned to best suit the patient's anatomy. The patient-specific cuts are identified by a surgeon or other medical professional pursuant to a preoperative plan, as described herein and set forth in FIG. 8. The femur 210 can be cut through the cutting slot 102, as well as by using any suitable cutting guide, such as a 4-in-1 cut guide or a 6-in-1 cut guide.

The cut guide is mounted to the femur 210 using fixation members or pins 120 and 122, which are illustrated in FIG. 5. The fixation pins 120 and 122 are custom set using the femoral positioning jig 10 in order to mount the cut guide at positions that will provide patient-specific cuts. The fixation pins 120 are guided to the femur 210 through the guide members 40 extending through each one of the first and second distal alignment members 22 and 24, as illustrated in FIG. 5 (only one of the pins 120 is illustrated). The pins 120 can be inserted into the femur 210 to form holes in the femur 210, removed from the holes of the femur 210 to allow the femur 210 to be cut through the cutting slot 102, and then be placed back into the holes in the femur 210 that the pins 120 were previously seated in to mount the cut guide to the femur 210. One of the fixation pins 122 is guided to the femur 210 through the center bore 114 of the first anterior guide member 110, and the other fixation pin 122 is guided through the center bore 116 of the second anterior guide member 112 (only one of the pins 122 is illustrated). The femoral positioning jig 10 is removed after the fixation pins 120 and 122 are set, thereby allowing the cut guide to be coupled to the femur 210 with the fixation pins 120 and 122. To facilitate removal of the femoral positioning jig 10, the pins 120 and/or 122 can be removed from the femur 210 prior to removal of the jig 10, and then be reinserted into the holes of the femur 210 that the pins 122 were previously seated in after the femoral positioning jig 10 is removed.

Setting the position of the femoral positioning jig 10 will now be described. To set the location of the cutting slot 102 to make a distal cut in the femur 210 at the distal surface 216, one or both of the first and second distal alignment members 22 and 24 can be rotated such that the distal ends 60 and 70 respectively thereof extend further from the bone-facing surface 18, thereby moving the distal portion 14 of the femoral positioning jig 10 away from the distal surface 216 of the femur 210, which will move the cutting slot 102 closer to the distal surface 216 such that a cutting instrument inserted through the cutting slot 102 will remove less of the femur 210 at the distal surface 216 as compared to when the cutting slot 102 is more anterior to the distal surface 216.

To remove a greater portion of the femur 210 at the distal surface 216, the first and second distal alignment members 22 and 24 can be rotated such that they are closer to the bone-facing surface 18, thereby allowing the distal portion 14 to be moved closer to the distal surface 216, which moves the cutting slot 102 superiorly and away from the distal or inferior surface 216. Therefore, cutting instruments inserted through the cutting slot 102 will remove a greater portion of the distal surface 216.

To set the varus and valgus angles, the first and second distal alignment members 22 and 24 can be set to extend from the bone facing surface 18 at different distances, thereby setting the distal portion 14 at an angle relative to the distal or inferior surface 216 of the femur 210. Accordingly, the cutting slot 102 will be set at a corresponding angle. For example, if the first distal alignment member 22 is medial of the second distal alignment member 24, and the femur 210 is of the patient's right leg, rotating the first distal alignment member 22 such that it extends further from the bone-facing surface 18 than the second distal alignment member 24 does, the cutting slot 102 will be angled away from the patient's midline, thus increasing the valgus angle. The fixation pins 120 and 122 will also be angled away from the patient's midline, thereby causing the cutting block mounted thereto to be angled away from the patient's midline. If the second distal alignment member 24 is positioned to extend further from the bone-facing surface 18 than the first distal alignment member 22, the cutting slot 102 will be angled towards the patient's midline, as will be the fixation pins 120 and 122 to angle the cutting block towards the patient's midline.

To set the angle of rotation, the first and the second posterior alignment members 54 and 56 can be selectively positioned. For example, if the first posterior alignment member 54 is medial of the second posterior alignment member 56, then arranging the first posterior alignment member 54 such that it extends less from the posterior portion 16 than the second posterior alignment member 56 will result in the cutting slot 102 and the fixation pins 120 and 122 being externally rotated. If the first and the second posterior alignment members 54 and 56 are arranged such that the first posterior alignment member 54 extends further than the second posterior alignment member 56, then the cutting slot 102 and the fixation pins 120 and 122 will be internally rotated.

With reference to FIGS. 6 and 7, a tibial positioning jig according to the present teachings is illustrated at reference numeral 310. The tibial positioning jig 310 generally includes a base 312. The base 312 includes a first or anterior portion 314 and a second or superior portion 316. The anterior portion 314 and the superior portion 316 can be arranged at any suitable angle relative to each other, such as generally at a right angle as illustrated. The base 312 defines a cutting slot 318 at any suitable position to cut a superior surface of a tibia, such as at the anterior portion 314. The tibial positioning jig 310 can be used in a total knee replacement, or in a revision procedure.

The tibial positioning jig 310 includes a first superior alignment member 320 and a second superior alignment member 322. The first and the second superior alignment members 320 and 322 are each threaded, so as to cooperate with threads of the superior portion 316. The superior portion 316 defines a slot or clearance 328 between the first and the second superior alignment members 320 and 322, which provides a clearance for ligaments. The tibial positioning jig 310 also includes first and second anterior alignment members 324 and 326, which are threaded to cooperate with threads of the anterior portion 314.

Each one of the first and the second superior alignment members 320 and 322, as well as the first and the second anterior alignment members 324 and 326, can be substantially similar to, or identical to, the first distal alignment member 22 described above. Therefore, the description of the first distal alignment member 22 is also sufficient to describe each one of the first and the second superior alignment members 320 and 322, and each one of the first and the second anterior alignment members 324 and 326. Each one of the first and the second superior alignment members 320 and 322, and each one of the first and the second anterior alignment members 324 and 326, thus include position indicators 42 and guide members 40 defined as a center bore configured to accommodate superior fixation pins 330 and 332 therethrough.

With reference to FIG. 7, the tibial positioning jig 310 is illustrated seated on a tibia bone 410. The tibia 410 includes a posterior surface 412, an anterior surface 414, and a tibial plateau 416. The tibial positioning jig 310 is arranged such that the superior portion 316 is opposite to the tibial plateau 416, and the anterior portion 314 is opposite to the anterior surface 414.

The tibial positioning jig 310 is orientated using the first and the second superior alignment members 320 and 322, as well as the first and the second anterior alignment members 324 and 326, in a manner similar to that described above with respect to the femoral positioning jig 10. For example, the first and the second superior alignment members 320 and 322 can be used to set the superior/inferior position of a bone cut, or cut depth, made through the slot 318. Rotating the first and the second superior alignment members 320 and 322 such that they extend further from the superior portion 316 will result in the bone cut through slot 318 being moved superiorly, because the slot 318 will be moved superiorly. The fixation pins 332 will also be moved superiorly, thereby positioning a bone cut block mounted thereto in a superior orientation. Rotating the first and the second superior alignment members 320 and 322 such that distal ends thereof are moved closer to the superior portion 316 will move in the inferior direction the slot 318, the corresponding bone cut therethrough, and the fixation pins 332. The first and the second superior alignment members 320 and 322 can be selectively and individually positioned to vary the angles of the fixation pins 330 and 332, which will vary the varus/valgus orientation of the bone cut block mounted thereto, and the varus/valgus orientation of the final tibial implant.

The first and the second anterior alignment members 324 and 326 can be used to set the medial to lateral position of the final tibial implant, as well as the rotational angle thereof. For example, rotating the first and the second anterior alignment members 324 and 326 such that they extend further from the anterior portion 314 will move the tibial positioning jig 310 in the anterior position, which will result in the bone cut block being positioned more anteriorly, the bone cuts being moved anteriorly, and the final tibial implant being moved anteriorly. Rotating the first and the second anterior alignment members 324 and 326 so that distal ends thereof are moved closer to the anterior portion 314 will allow the tibial positioning jig 310 to be moved in the posterior direction, which will result in the bone cut block being positioned more posteriorly, the bone cuts being moved posteriorly, and the final tibial implant being moved posteriorly. The first and the second alignment members 324 and 326 can be selectively positioned to vary the rotational angle of the final tibial implant, by varying the position of the superior fixation pins 330, which will vary the rotational angle of the bone cut block mounted thereto.

Figure 8:
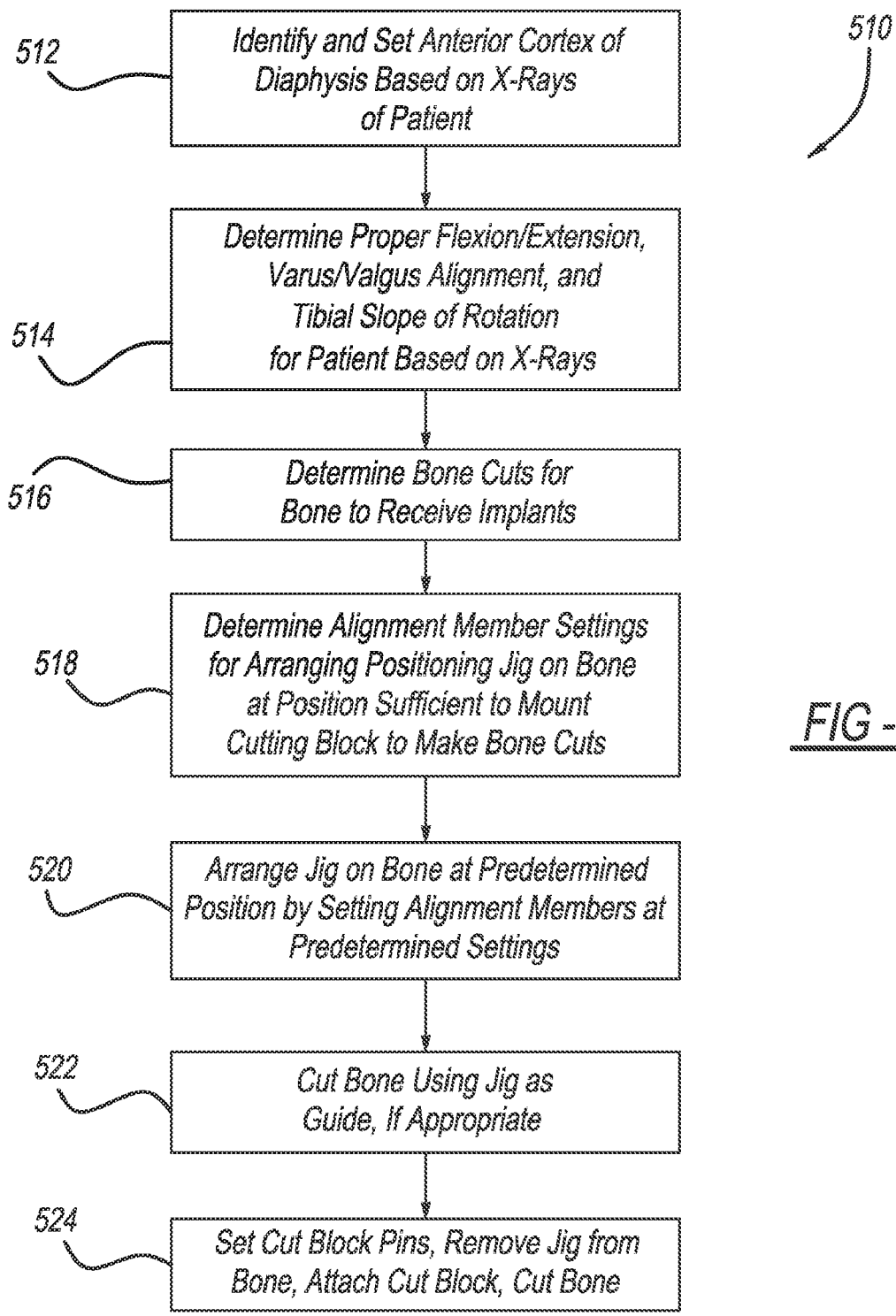
FIG. 8 is a flowchart illustrating steps included in developing a preoperative plan for use of the positioning jigs, and use of the positioning jigs to cut bone.

With additional reference to FIG. 8 and the flowchart at reference numeral 510, determination of the settings of each of the alignment members 22, 24, 54, 56, 320, 322, 324, and 326 to provide the femoral positioning jig 10 and the tibial positioning jig 310 with patient-specific orientations without use of an intramedullary rod will now be described. With initial reference to block 512, a physician or other suitable healthcare professional identifies the anterior cortex of the diaphysis of the patient's femur. Proper flexion/extension, varus/valgus alignment, and tibial slope of rotation of the patient's knee is then determined based on the patient's x-rays at block 514. At block 516, the physician or other suitable healthcare personnel determines the bone cuts necessary in the patient's femur 210 to receive a femoral implant, and optionally the patient's tibia 40 if the patient is to receive a tibial implant. The type, position, and orientation of the bone cuts will depend on the patient's anatomy. For example, if the patient's natural knee has a generally valgus orientation, then bone cuts to recreate the valgus orientation will be used.

With reference to block 518, the physician, suitable healthcare professional, or other suitable person, entity, or device, will determine the settings of the alignment members 22, 24, 54, 56, 320, 322, 324, and/or 326 necessary to arrange the femoral positioning jig 10 and/or the tibial positioning jig 310 at positions sufficient to guide one or more cutting instruments to the femur 210 and/or tibia 410 to make the necessary bone cuts through slots 102 or 318, and arrange the fixation pins 120, 122, 330 and/or 332 to arrange suitable cut blocks for making additional cuts to the femur 210 and/or the tibia 410. The femoral and tibial positioning jigs 10 and 310 can both be used in a total knee replacement, or individually if only a femoral or tibial implant is appropriate.

With additional reference to block 520, the femoral positioning jig 10 and/or the tibial positioning jig 310 are respectively arranged on the femur 210 and the tibia 410 at predetermined positions by setting the alignment members 22, 24, 54, 56, 320, 322, 324, and/or 326 at the predetermined settings identified at block 518. With reference to block 522, the femur 210 and/or the tibia 410 are cut with any suitable cutting instrument using the slot 102 of the femoral positioning jig 10 and/or the slot 318 of the tibial positioning jig 310 if appropriate. With reference to block 524, the fixation pins 120, 122, 330 and 332 are set into the femur 210 and/or tibia 410 as described above, the femoral and tibial positioning jigs 10 and 310 are removed from the femur 210 and tibia 410, suitable cut blocks are attached to the fixation pins 120, 122, 330 and/or 332, and the femur 210 and/or tibia 410 are cut using any suitable cutting instrument guided to the femur 210 and/or tibia 410 by the cut blocks.

The present teachings thus provide for a patient-specific femoral positioning jig 10 and tibial positioning jig 310, for guiding cutting instruments to provide patient-specific bone cuts based on x-rays of the patient, which are less costly and more readily attainable than more complex three dimensional imaging, such as CT scans and MRIs. These patient-specific bone cuts can be made without the need of an intramedullary rod.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for positioning a guide relative to a knee bone of a patient, the system comprising:
    a base having a knee bone-facing surface and an opposing second surface; and
    at least one alignment member configured to be moveably received by the base so as to be moveable towards and away from the knee bone to adjust a spacing of the base relative to the knee bone to achieve a desired positioning for the base relative to the knee bone, wherein the at least one alignment member is configured to be set at a predetermined alignment member setting corresponding to the desired positioning for the base with position indicia indicating such setting and optional variations of such setting, wherein the desired positioning is based on one or more x-rays of the patient that identify patient specific characteristics of the knee bone including one or more of the anterior cortex of the diaphysis of a femur, a flexion/extension gap, and a desired varus/valgus alignment.

2. The system of claim 1, wherein the base is configured to define at least one slot or aperture to facilitate resection of the knee bone or placement of a fixation pin in the knee bone.

3. The system of claim 2, wherein the at least one alignment member defines a guide member configured to direct the fixation pin to the knee bone in a patient-specific location as determined by the x-rays of the patient.

4. The system of claim 3, wherein the guide member is a through bore defined by the at least one alignment member.

5. The system of claim 1, further comprising a guide portion configured to be moveably received in the base so as to be adjustable relative to the base and knee bone, wherein the guide portion defines a cutting slot configured to direct a cutting member to the knee bone.

6. The system of claim 5, wherein the base includes a first part configured to face a distal portion of the knee bone and a second part configured to face a posterior portion of the knee bone, and wherein the guide portion is configured to face an anterior portion of the knee bone when mounted on the base such that the knee bone is surrounded by the guide on at least three sides thereof.

7. The system of claim 6, wherein any one of the first part of the base, the second part of the base and the guide portion can receive the at least one alignment member therein.

8. The system of claim 1, wherein the least one alignment member is configured to move toward the knee bone when rotated in a first direction, and move away from the knee bone when rotated in a second direction that is opposite to the first direction.

9. The system of claim 1, wherein the least one alignment member is configured to move toward the knee bone when rotated in a first direction, and move away from the knee bone when rotated in a second direction that is opposite to the first direction.

10. A system for positioning a guide relative to a knee bone of a patient, the system comprising:
 a base having a knee bone-facing surface and an opposing second surface; and
 at least one alignment member configured to be moveably received by the base so as to be moveable towards and away from the knee bone to adjust a spacing of the base relative to the knee bone to achieve a desired positioning for the base relative to the knee bone, wherein the at least one alignment member is configured as a dial including a position indicator that identifies a rotational position of the at least one alignment member, wherein the position indicator has a neutral position that corresponds to the desired positioning for the base, wherein the desired positioning is based on one or more x-rays of the patient that identify patient specific characteristics of the knee bone including one or more of the anterior cortex of the diaphysis of a femur, a flexion/extension gap, and a desired varus/valgus alignment, and wherein the at least one alignment member defines a guide member configured to direct the fixation pin to the knee bone in a patient-specific location as determined by the x-rays of the patient.

11. The system of claim 10, wherein the guide member is a through bore defined by the at least one alignment member.

12. The system of claim 10, wherein the at least one alignment member is a dial including a position indicator that identifies a rotational position of the at least one alignment member, wherein the position indicator has a neutral position that corresponds to the desired positioning for the base.

13. The system of claim 10, further comprising a guide portion configured to be moveably received in the base so as to be adjustable relative to the base and knee bone, wherein the guide portion defines a cutting slot configured to direct a cutting member to the knee bone.

14. The system of claim 13, wherein the base includes a first part configured to face a distal portion of the knee bone and a second part configured to face a posterior portion of the knee bone, and wherein the guide portion is configured to face an anterior portion of the knee bone when mounted on the base such that the knee bone is surrounded by the guide on at least three sides thereof.

15. The system of claim 14, wherein any one of the first part of the base, the second part of the base and the guide portion can receive the at least one alignment member therein.

16. A system for positioning a guide relative to a knee bone of a patient, the system comprising:
 a base having a knee bone-facing surface and an opposing second surface; and
 at least one alignment member configured to be moveably received by the base so as to be moveable towards and away from the knee bone to adjust a spacing of the base relative to the knee bone to achieve a desired positioning for the base relative to the knee bone, wherein the at least one alignment member is configured to be set at a predetermined alignment member setting corresponding to the desired positioning for the base with position indicia indicating such setting and optional variations of such setting, wherein the desired positioning is based on one or more x-rays of the patient that identify patient specific characteristics of the knee bone including one or more of the anterior cortex of the diaphysis of a femur, a flexion/extension gap, and a desired varus/valgus alignment, and wherein the base includes a first part configured to face a distal portion of the knee bone and a second part configured to face a posterior portion of the knee bone.

17. The system of claim 16, further comprising a guide portion configured to be moveably received in the base so as to be adjustable relative to the base and knee bone, wherein the guide portion defines a cutting slot configured to direct a cutting member to the knee bone.

18. The system of claim 17, wherein the guide portion is configured to face an anterior portion of the knee bone when mounted on the base such that the knee bone is surrounded by the guide on at least three sides thereof.

19. The system of claim 18, wherein any one of the first part of the base, the second part of the base and the guide portion can receive the at least one alignment member therein.

* * * * *